(12) United States Patent
Ruf et al.

(10) Patent No.: US 8,690,581 B2
(45) Date of Patent: Apr. 8, 2014

(54) OPTHALMOSCOPE SIMULATOR

(75) Inventors: Thomas Ruf, Mannheim (DE); Markus Schill, Heidelberg (DE); Clemens Wagner, Heidelberg (DE)

(73) Assignee: Vrmagic GmbH, Mannheim (DE)

( * ) Notice: Subject to any disclaimer, the term of this patent is extended or adjusted under 35 U.S.C. 154(b) by 403 days.

(21) Appl. No.: 12/737,063

(22) PCT Filed: Jun. 10, 2009

(86) PCT No.: PCT/EP2009/057216
§ 371 (c)(1),
(2), (4) Date: Dec. 3, 2010

(87) PCT Pub. No.: WO2009/150190
PCT Pub. Date: Dec. 17, 2009

(65) Prior Publication Data
US 2011/0091856 A1    Apr. 21, 2011

(30) Foreign Application Priority Data
Jun. 11, 2008   (DE) .......................... 10 2008 027 832

(51) Int. Cl.
*G09B 23/28* (2006.01)

(52) U.S. Cl.
USPC .......................................... 434/271; 434/262

(58) Field of Classification Search
USPC ........... 434/262–275; 351/205, 214, 220–221
See application file for complete search history.

(56) References Cited

U.S. PATENT DOCUMENTS

| 4,684,227 A | 8/1987 | Schmidt et al. |
| 4,786,154 A | 11/1988 | Fantone et al. |

(Continued)

FOREIGN PATENT DOCUMENTS

| DE | 36 27 251 A1 | 2/1988 |
| DE | 87 04 606.7 U1 | 9/1988 |

(Continued)

OTHER PUBLICATIONS

"Contextual Anatomic Mimesis", Bichlmeier et al., IEEE 2007, 10 pgs.

(Continued)

*Primary Examiner* — Timothy A Musselman
(74) *Attorney, Agent, or Firm* — Hudak, Shunk & Farine Co. LPA

(57) ABSTRACT

An ophthalmoscope simulator for simulation and a method for simulation of the handling of an ophthalmoscope, having a support that can be attached to a head of an observer, at least one first imaging display disposed on said support, wherein the display can be placed in front of an eye of the observer for displaying a virtual reality, an ophthalmoscope dummy that can be supported by one hand of the observer, a position recognition system for determining the spatial position and/or orientation of the support and of the ophthalmoscope dummy and a computer for displaying an image of an environment, a patient head and/or at least a portion of the ophthalmoscope dummy on the display. In particular, a patient head dummy is provided that comprises at least one peripheral surface with a patient eye position defined therein, wherein the spatial position and/or orientation of the patient head dummy can be determined and displayed by way of the position recognition system and that in addition to or alternative to the ophthalmoscope dummy an image portion can be added to the image displayed to the observer, wherein the image portion represents a virtual retina as could selectively appear to the observer, taking into account the spatial position of the support, the ophthalmoscope dummy and the patient head dummy.

18 Claims, 2 Drawing Sheets

(56) References Cited

U.S. PATENT DOCUMENTS

| | | |
|---|---|---|
| 4,963,014 A | 10/1990 | Heine et al. |
| 5,543,886 A | 8/1996 | Suda |
| 5,815,241 A | 9/1998 | Heine et al. |
| 6,350,031 B1 | 2/2002 | Lashkari et al. |
| 6,847,336 B1 | 1/2005 | Lemelson et al. |
| 2005/0203367 A1 | 9/2005 | Ahmed et al. |

FOREIGN PATENT DOCUMENTS

| | | |
|---|---|---|
| DE | 39 19 181 C1 | 9/1990 |
| DE | 296 13 549 U1 | 11/1996 |
| DE | 102 42 983 A1 | 3/2004 |
| DE | 103 36 475 A1 | 3/2005 |
| DE | 10 2004 050 807 A1 | 9/2005 |
| DE | 20 2005 007 013 U1 | 11/2005 |
| DE | 10 2005 011 781 A1 | 9/2006 |
| DE | 10 2008 027 832 A1 | 12/2009 |
| EP | 0 048 181 A2 | 3/1982 |
| EP | 0 738 123 | 10/1996 |
| EP | 1 369 769 A2 | 12/2003 |
| WO | WO 99/60529 A1 | 11/1999 |

OTHER PUBLICATIONS

"Modeling Real Objects Using Video See-Through Augmented Reality", Lee et al., Presence: vol. 11, No. 2, Apr. 2002, pp. 144-157.

"Augmented Reality Guidance for Needle Biopsies: A Randomized, Controlled Trial in Phantoms", Rosenthal, et al., University of North Carolina at Chapel Hill, Departments of Computer Science, Radiology and Biostatistics, 2001, 9 pgs.

"Dynamic Virtual Convergence for Video See-Through Head-Mounted Displays: Maintaining Maximum Stereo Overlap throughout a Close-range Work Space", State et al., Universit of North Carolina at Chapel Hill, Feb. 2001, 10 pgs.

Lee, D, et al., "Ophthalmoscopic Examination Training Using Vertual Reality", Virtual Reality, Bd. 4, Nr. 3, Sep. 1999, Seiten, pp. 184-191 (XP002553166).

Sautter, V., et al. "Ophthalmoskipie", pp. 258-296.

OPTHALMOSCOPE SIMULATOR

CROSS-REFERENCE

This is a national phase application of PCT/EP2009/057216, filed Jun. 10, 2009, which claims priority to DE 10 2008 027 8327, filed Jun. 11, 2008.

FIELD OF THE INVENTION

The invention relates to an ophthalmoscope simulator for simulation of the manual manipulation of an ophthalmoscope, comprising:
- a holding means which can be applied to the head of an observer, which holding means bears at least one first image display, which display can be positioned ahead of one eye of the observer for representation of a virtual reality,
- a position recognition system whereby the spatial position and/or orientation or relative position of the holding means is determinable and can be tracked, and
- a computer whereby an image of the surroundings and/or of a patient head can be displayed to the observer via the display means, taking into account the relative position.

BACKGROUND OF THE INVENTION

The invention also relates to a method of operating such an ophthalmoscope simulator.

A simulator for simulating the manual manipulation of a direct ophthalmoscope is already known, from the journal article "Ophthalmoscopic examination training using virtual reality", of D. Lee et al. (1999 Virtual Reality, 4, 184-191, pub. Springer Verlag London Ltd.). The simulation system is comprised of a 3D mouse whereby the observer can move a virtual cone of light of a simulated direct ophthalmoscope relative to a patient head displayed on a display screen. Alternatively, 3D goggles or a head-mounted display are/is provided by means of which the patient head and a cone of light which can be produced on the patient head by an ophthalmoscope, as well as a retina, are displayable to the observer. The display is tracked via a position recognition system, so that either the relative position between the mouse (the ophthalmoscope light cone) and the display screen or the visualized patient head, or the absolute position of the head-mounted display, is displayable to the observer. The virtual scene in this case is completely rendered on the display, without additional frames of reference and without additional hand-held sensors.

The priority document DE 10 2008 027832 A1 incorporates parts of the concept of this reference, but goes beyond that disclosure. The determination of the relative position between the mouse and the head-held display is not included [in said reference]. Therefore, for the purpose of improving upon the intuitive manipulation, the use of an ophthalmoscope is proposed (p. 190 Col. 1 Para. 2). Alternatively, it is proposed that all hand-held sensors (thus the mouse or an ophthalmoscope) be eliminated, and an HMD [(head-mounted display)] be employed which will completely render the scene without other frames of reference (p. 190 Col. 1 Paras. 3-4).

US 2005/0203367 A1 describes an interactive instrument for operating a representation system for CT data, wherein an image component is inserted in the image of a real scene. The real image is that of the head of a patient who is to undergo surgery. Via the described system comprised of the HMD, a pen, and a computer, the CT data made available are superposed over a 3D representation of the real image. The observer thus sees both the real image and the virtual CT data. The pen and the HMD are tracked, so that by means of the pen one can operate an also displayable interactive switching surface for controlling the representation of the CT data. The spatial arrangement of the CT data visualization is determined in relation to six points located on the fixed patient head. The points must be entered by the user by means of the tracked pen, in order to determine the positions of said points. For this purpose the sequence of positions and the actual individual positions of the said points on the patient head must be known. The patient head itself must be registered. The said points serve as a fixed "anchor" for the simulation of the CT data. In the event that the patient head is moved, this will cause loss of the necessary spatial correlation between the CT data and the patient head.

SUMMARY OF THE INVENTION

The underlying problem of the present invention is to devise an ophthalmoscope simulator which provides a maximally realistic simulation of an eye examination.

This problem is solved according to the invention in that an ophthalmoscope dummy which can be held by one hand of the observer is provided, along with a patient head dummy which has at least one peripheral surface bearing a patient eye position, wherewith by means of the position recognition system the relative spatial position and/or orientation of the ophthalmoscope dummy and/or of the patient head dummy can be detected and can be displayed on the display, via the computer; and an image component can be superposed, or rendered, in the image displayed to the observer, in addition to or alternatively to [the image of] the ophthalmoscope dummy, wherewith the image component represents a virtual retina as it would appear to the observer, selectively taking into account the spatial position of the holding means, the ophthalmoscope dummy, and the patient head dummy. Alternatively, via the image component also the surroundings, the patient dummy, and/or the ophthalmoscope, or at least a part thereof which deviates from the real scene, can be displayed in changed form.

The underlying problem is also solved in that, by means of the position recognition system, the spatial position and/or orientation of the ophthalmoscope lens dummy, the patient head dummy, and the holding means can be determined and tracked, and that an image of the surroundings, a patient head, and/or the ophthalmoscope dummy can be displayed on the display or screen (e.g. an OLED (organic light emitting diode) or an LCD (liquid crystal display), wherewith in the image an image component is superposed or rendered in addition to or alternatively to the image of the ophthalmoscope dummy, which image component virtually represents the retina in the manner in which it would appear to the observer, selectively under consideration of the relative spatial positions between the holding means, the ophthalmoscope dummy, and the patient dummy. If an image of a virtual patient head is represented, this is caused to coincide spatially with the image of the ophthalmoscope dummy. Thus during the operation of the system the ophthalmoscope lens dummy, the patient dummy, the holding means, and the HMD are tracked to take into account their mutual relative positions.

It is an important feature of the invention that, in addition to the holding means which provides the position and orientation of the head of the observer, a dummy for the ophthalmoscope (ophthalmoscope lens) and a dummy for a patient head are provided, wherewith, via the position recognition system, the relative mutual spatial positions of the aforesaid three objects are known at any time. Via the displays, the surroundings as they would appear to the observer depending on his head position are displayed to the observer, wherewith the position of the ophthalmoscope dummy held by the observer and the position of the patient head dummy are displayed and may be superposed on the display. Thus the surroundings and the patient head and the ophthalmoscope dummy can be visualized and displayed in any desired manner, e.g. as a real image or a virtual image. The virtual image of the patient head may be brought into spatial correspondence with the real image of the patient head dummy. Regarding the ophthalmoscope dummy, in the case of an ophthalmoscope lens an image component is superposed which would be produced if the observer in reality would see one through an ophthalmoscope lens. Thus, preferably the observer sees the surroundings behind the lens as being strongly magnified and upside down. Only in the case in which he brings the ophthalmoscope dummy into the correct relative position between the holding means and the patient head dummy is there displayed to him as the image component a virtual image of a retina such as he would see in reality.

The position recognition system has generally a basis which is located on the holding means or on the patient head dummy. Alternatively, it also may be located separately in space. In the first two cases, the scene to be rendered is substantially smaller, which allows higher tracking speed and higher quality. The position recognition occurs as a rule through one or more markers which are disposed on the object to be recognized, thus the ophthalmoscope dummy or the patient head dummy. The position recognition system is preferably optical, i.e. the basis has corresponding cameras, e.g. video cameras, by which the markers and their positions can be detected. If a complex position recognition system is used it is possible to dispense with the markers on the objects. Through the use of markers, however, the system can be substantially simplified, particularly for determination of the position and orientation of the patient head dummy and the peripheral surface around the eye position, which preferably models the shape of a human face. The basis will typically make use of two cameras, but it is also possible to use only one camera to recognize the markers for the purpose of subsequent determination of their positions or tracking.

Further, it may be advantageous, if at least one video camera is provided on the holding means, to produce video images of the real surroundings, wherewith through the video image a part of the surroundings, such as the patient head dummy, the hand of the observer, the ophthalmoscope dummy, and/or a part thereof, can be displayed on the display. In this connection, the position recognition system can be used to determine the spatial position and/or orientation of the video camera at least indirectly via the holding means. This video camera is provided in addition to the video cameras of the position recognition system.

In this case, the image which appears to the observer is comprised of images of the real surroundings disposed ahead of the observer, plus superposed image components. The real surroundings comprise, in addition to the patient head dummy ahead of the observer, the observer's hand which is holding the ophthalmoscope dummy, the ophthalmoscope dummy, and the laboratory surroundings around these items. The superposed image component comprises that which the observer would see through the ophthalmoscope lens or ophthalmoscope which he is holding if the actual instrument were there. In the case of an ophthalmoscope lens dummy, the display will contain the edge of the dummy being held by the observer, wherewith the interior image component, in the location where with the use of an ophthalmoscope lens the glass body is located, a corresponding magnified but upside down image will appear which contains the real or virtual subject behind the ophthalmoscope lens dummy. This may also be a part of the surroundings or of the patient head dummy. In the case in which the relative position between the head of the observer (thus the holding means) and the ophthalmoscope dummy and the patient head dummy meets certain predetermined requirements which simulate reality, as to the angles and distances, there will be displayed to the observer as an image component the image of a virtual retina, such as would occur in practice. Also, the edge of the virtual ophthalmoscope lens and/or a peripheral part of a virtual patient head can be superposed.

In this connection it may be provided that the ophthalmoscope dummy is a dummy for a lens of an indirect ophthalmoscope or a dummy for a lens of a direct ophthalmoscope. In the case of a dummy for an indirect ophthalmoscope lens, the observer, as in the case of an actual examination, can support the hand with which he holds the ophthalmoscope dummy, against the peripheral surface around the eye position on the patient head dummy. In the other case, where the ophthalmoscope dummy is a dummy for a direct ophthalmoscope, the ophthalmoscope dummy will be held directly ahead of the observers eye and ahead of the display, e.g. the HMD, head-mounted display. In this case one does not have a good simulation close to reality of the tactile relationship to the patient head.

Further, it may be advantageous if the holding means, the video camera, the ophthalmoscope dummy, the patient head dummy, the patient eye position, and/or the peripheral surface bear(s) one and preferably three markers by which, via the position recognition system, to be able to determine the spatial position and/or orientation of the given object(s) relative to the position recognition system. The use of the one or more markers facilitates the determination of positions and orientations of the thus marked objects. A free position determination without the use of markers is possible but much more complex. When one determines the position of the holding means and HMD, the position and relative position of the head and eyes of the observer is also known. Additional markers for the head of the observer are not necessary but may be provided. The patient head dummy bears more than 3 markers, maximum 37. The use of a substantial number of markers allows one to optimally determine the position and orientation, and relative position, of the patient head dummy, which preferably resembles a human head.

It may also be advantageous if a second display is provided, with the first display being capable of being disposed ahead of the right eye and the second display being capable of being disposed ahead of the left eye of the observer, wherewith a distance a4 between the displays is adjustable, and wherewith a second video camera provides a display for the second display, with a distance a5 between the video cameras being adjustable. Thus the eye distance of the displays and the distance of the stereoscopic basis are both adjustable. The second video camera is in addition to the cameras of the position recognition system.

It may further be advantageous if means for simulating a light filter are provided. This allows conditions to be created for the observer which even more closely resemble reality.

Advantageously, means for representing a distance a1, a2, and/or a3, and/or means for representing a deviation of the distance a1, a2, and/or a3 from a set-point value are provided, with a1 being the distance between the holding means and the patient eye position, a2 being the distance between the ophthalmoscope dummy and the patient eye position, and a3 being the distance between the holding means and the ophthalmoscope dummy. For an un-practiced observer it is very difficult to find the correct relative position of the ophthalmoscope or ophthalmoscope lens and the dummy, in order to obtain the desired image of the retina. A display of the aforesaid distances will assist a trainee observer to reach the correct relative positions, and to maintain control over these positions during the examination. Starting from the position of the holding means, the position of the observer eye or of other parts of the holding means can be calculated and can be taken into account in the distances a1 and a3.

It may also be advantageous if the means comprise optical display means which are recognizable via the display, and if the computer has means for storage, retrieval, evaluation, and/or changing of the images and/or image components and for creation of a combination display of the regions which the observer has observed on the virtual retina during a simulated examination. In particular, the combination display or arrangement of the regions which the observer has seen during the simulated examination gives him an extremely important impression of the past manual manipulation and the observation path which he has gone through on the retina.

It also may be advantageous if the images, image components, and/or video images stored or changed in the computer can be displayed on the display means or on a separate monitor provided for the purpose. This allows a second person to simultaneously reproduce the optical impression which the observer is receiving.

Regarding the method, it may be advantageous if the image component which represents the retina is only superposed if the relative position between the holding means, the ophthalmoscope dummy, and the patient head dummy satisfies predefined conditions. Only when the observer places the ophthalmoscope dummy in such a manner as would be necessary in a real situation with an ophthalmoscope lens or a direct ophthalmoscope in order to be able to see the retina, will the corresponding image component be superposed. In selecting what image component representing the retina will be displayed, the relative position of the ophthalmoscope dummy is taken into account. In this connection, a corresponding source or collection of image components from a retina may be provided.

Regarding the method, it may also be advantageous if the video camera renders a video picture of the real surroundings, such as the patient head dummy, the observer's hand, the ophthalmoscope dummy and/or a part of it, and displays same on the display. This gives rise to the abovementioned advantages concerning the structure of the image displayed to the observer, comprised of the real surroundings located ahead of him and certain superposed image components which are virtual parts.

Correspondingly, it may be advantageous if the distance a1 between the holding means and the patient eye position and/or the distance a2 between the ophthalmoscope dummy and the patient eye position and/or the distance a3 between the holding means and the ophthalmoscope lens dummy, and/or a deviation of the respective distances a1, a2, a3 from a set-point value, is/are displayed to the observer. Additionally or alternatively, other parameters of the relative position between the holding means, and the head of the observer, and the ophthalmoscope dummy and/or the patient head dummy, e.g. various angles of inclination of the ophthalmoscope dummy, or the angle of view of the observer, or the deviations of these parameters from respective set-point values, can be appropriately displayed. The angles of inclination may comprise, in particular, the rotational angles around an axis perpendicular to the optical axis of the simulated ophthalmoscope dummy or of the optics.

It may further be advantageous if images are computed for the position and/or movement of the holding means and/or the ophthalmoscope dummy, which reproduce a view from at least one other viewpoint in space. This allows, e.g., display of movements carried out by the observer from another viewpoint in space, e.g. a position lateral to the observer. This allows the observer to retroactively obtain an impression of his positional and movement behavior.

It may additionally be advantageous if eye movements of the patient are simulated. Because patients frequently execute eye movements in the nature of changing of the direction of view or blinking, for the purpose of training it may be helpful to be able to simulate such movements.

The underlying problem of the invention is also solved by a computer system or data storage medium and/or a computer program, for carrying out the above-described method.

BRIEF DESCRIPTION OF THE DRAWINGS

Additional features and advantages of the invention are disclosed in the patent claims, Specification, and drawings.

DETAILED DESCRIPTION OF THE INVENTION

Figure 1:
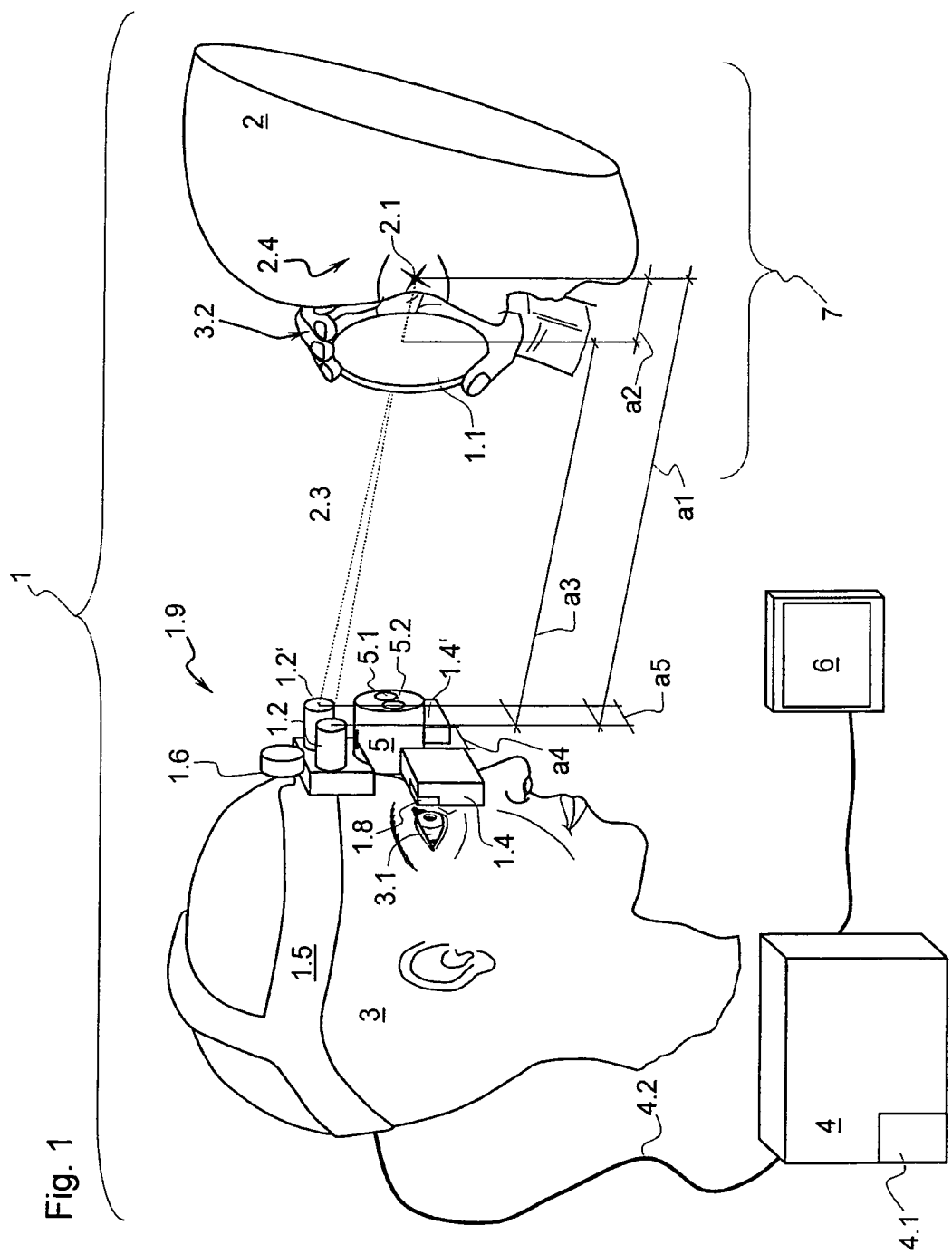
FIG. 1 is a main schematic drawing illustrating an ophthalmoscope simulator for an indirect ophthalmoscope.

The ophthalmoscope simulator 1 illustrated in FIG. 1 is comprised of a holding means 1.5 which can be set upon the head of an observer 3 and on which essentially a first display 1.4 and a second display 1.4' are disposed. The display devices 1.4 and 1.4' are associated with two video cameras 1.2, 1.2' which register the scene. Such an aggregate is also called a "head-mounted display" (HMD) 1.9. The HMD 1.9 also is comprised of a base 5 of a position-determining system having two video cameras 5.1, 5.2 as the basis for optical tracking. The thus equipped HMD 1.9 is connected via a connecting line 4.2 to a computer 4, image processing unit. The image processing unit 4 has means 4.1 for storing, retrieving, evaluating, and/or changing of images 1.3 or parts of images 2.2, and for generating a combination of various images 1.3, 2.2. A monitor 6 is connected to the computer 4; the images 1.3 present on the displays 1.4 and 1.4' can also be displayed on this monitor.

It is also possible to display other images, such as a view from a different viewpoint in space.

The HMD 1.9 rests on the head 3 of the observer, so that the two displays 1.4, 1.4' and the two display screens are positioned ahead of the respective eyes 3.1 of the observer. The distance a4 between the two screens 1.4, 1.4' is variable so that it can be adjusted to the distance between the eyes of the observer.

The ophthalmoscope simulator 1 also has an ophthalmoscope lens dummy 1.1 which is held and positioned by means of the hand of the observer 3.2. An additional part of the ophthalmoscope simulator 1 is a patient head dummy 2 in the form of a head and face. The patient head dummy 2 has a position 2.1 simulating the eye opening of the patient being examined, and a peripheral surface 2.4 surrounding the position 2.1.

The ophthalmoscope lens dummy 1.1, similarly to an ophthalmoscope lens of an indirect ophthalmoscope, can be placed by the hand 3.2 of the observer ahead of the patient eye being observed, the position 2.1. The HMD 1.9 thus comprises the head-held part of an indirect ophthalmoscope, with which by means of a corresponding holding means 1.5 an observer optical system is positioned ahead of the observer eye 3.1.

Figure 2A:
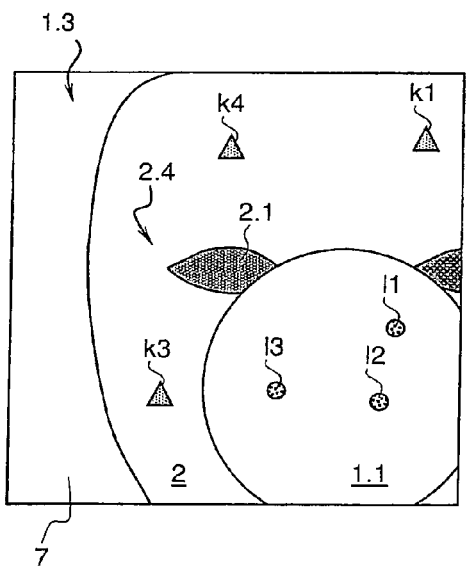
FIG. 2a is representation of a view of surroundings with a patient head dummy and an ophthalmoscope lens dummy.
Figure 2B:
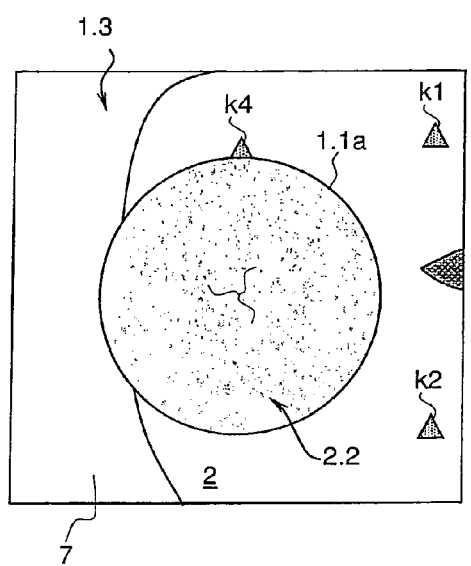
FIG. 2b is a representation according to FIG. 2a with a superposed image component of a retina.
Figure 2C:
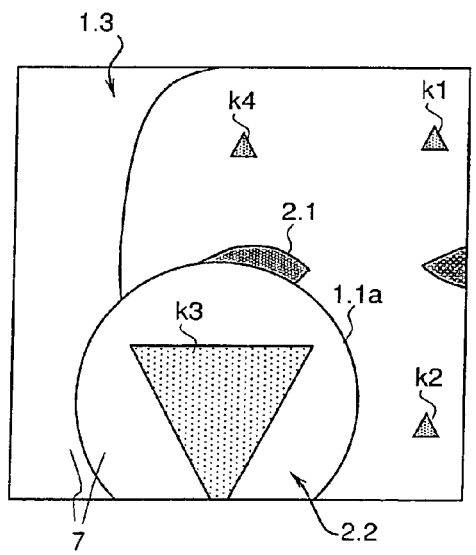
FIG. 2c is a representation according to FIG. 2b with a superposed image component of the surroundings.

The image 1.3 of the ophthalmoscope lens dummy 1.1 obtained via the two video cameras 1.2, 1.2', and the images of the patient head dummy 2 and its surroundings 7, are displayed to the observer via the display screens 1.4, 1.4' in a manner illustrated in FIGS. 2a to 2c.

Via the base of the position-determining system 5, the relative position of the ophthalmoscope lens dummy 1 and the patient head dummy 2, with respect to the HMD 1.9 can be determined and can thus be virtually represented and superposed on a given image.

Within the displays 1.4, 1.4', optical display means 1.8 are provided which display to the observer the distances a1 to a3, and any deviation of these, among other things. The optical display means 1.8 are preferably a part of the display devices 1.4, 1.4'. Separate display means 1.8 are generally unnecessary. The HMD 1.9 also has other means 1.6 for simulating optical filters during the examination.

The image according to FIG. 2a which is displayed to the observer is comprised of the real picture of the environment, in particular the patient head dummy 2 and the ophthalmoscope lens dummy 1.1, imaged by the video cameras 1.2, 1.2'. For the sake of simplicity, images of the hand 3.2 of the observer and other objects in the wider surroundings 7 are omitted. In the video image 1.3 displayed to the observer the various markers k1, k3, and k4 of the patient head dummy 2 may be seen, along with the position of the patient eye 2.1. Further, the markers 11-13 of the ophthalmoscope lens dummy 1.1 may be seen. The surroundings 7 are seen laterally of the patient head dummy 2. According to a preferred embodiment, the markers are not visible but are located below a cover layer (not shown).

As soon as the observer brings the ophthalmoscope lens dummy 1.1 into the correct position ahead of the simulated patient eye, patient eye position 2.1, an image component 2.2 is imposed in place of the ophthalmoscope lens dummy; this image component partial image 2.2 shows a virtual picture of the retina such as the observer would see in real life. The image of the ophthalmoscope lens dummy 1.1 is largely replaced by the image component 2.2; preferably an edge 1.1a from the ophthalmoscope lens dummy 1.1 remains from the real image 1.3 of the video cameras 1.2, 1.2'.

Preferably it is also provided that a corresponding image component 2.2 can be superposed in place of the ophthalmoscope lens dummy 1.1 if the ophthalmoscope lens dummy 1.1 is not positioned in a position such as to provide an image of the retina. This is illustrated in FIG. 2c. The ophthalmoscope lens dummy 1.1 is in this case positioned in the region of the marker k3, and displays this marker to the observer in an image which is enlarged and upside down. In this case, a real representation of the ophthalmoscope lens dummy 1.1 according to FIG. 2a is not needed. The observer can see, instead of the ophthalmoscope lens dummy 1.1, the corresponding real or virtual image component 2.2 representing the retina or otherwise, depending on whether the ophthalmoscope lens dummy 1.1 is directed correctly or not.

Figure 3:
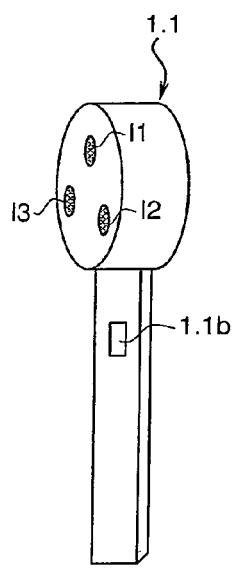
FIG. 3 is a dummy of a direct ophthalmoscope.

According to another embodiment it is provided that, instead of simulation of an indirect ophthalmoscope wherein the observer manipulates by hand an ophthalmoscope lens dummy 1.1, a direct ophthalmoscope is simulated which is in the form of a corresponding dummy 1.1 according to FIG. 3.

The dummy 1.1 of the direct ophthalmoscope has corresponding markers 11-13 which enable recognition of the position and orientation in space. Further, the dummy 1.1 has additional tactile means 1.1b enabling simulation of switches and/or other operating elements of a real direct ophthalmoscope.

LIST OF REFERENCE NUMERALS

1 Ophthalmoscope simulator.
1.1 Ophthalmoscope lens dummy.
1.1a Edge.
1.1b Tactile means.
1.2 Video camera.
1.2' Second video camera.
1.3 Image, video image.
1.4 First display, video display.
1.4' Second display, video display.
1.5 Holding means.
1.6 Means.
1.8 Means, optical display means.
1.9 Head-mounted display (HMD).
2 Patient head dummy.
2.1 Patient eye position.
2.2 Image component, image of the retina or image of the surroundings.
2.4 Peripheral surface.
3 Head.
3.1 Eye of observer, right eye.
3.2 Hand of observer.
4 Computer, image processing unit.
4.1 Means.
4.2 Connecting line.
5 Position recognition system, basis.
5.1 Video camera.
5.2 Video camera.
6 Monitor.
7 Surroundings.
a1-a5 Distances.
k1-k4 Markers.
11-13 Markers.

What is claimed is:

1. An ophthalmoscope simulator for simulation of the manual manipulation of an ophthalmoscope, comprising:
a support which can be applied to the head of an observer, which support bears at least one first image display, which display can be positioned ahead of one eye of the observer for representation of a virtual reality,
a position recognition system whereby a spatial position and/or orientation or relative position of the support is determinable, and
a computer whereby an image of the surroundings and/or of a patient head can be displayed to the observer via the at least one first image display;
wherein the simulator further comprises an ophthalmoscope dummy and a patient head dummy, wherewith the patient head dummy has at least one peripheral surface bearing a patient eye position, wherewith by the position recognition system the spatial position and/or orientation of the ophthalmoscope dummy and/or of the patient head dummy relative to the support can be determined; and wherein an image component can be superimposed in the image displayed to the observer, in addition to or alternatively to the image of the ophthalmoscope dummy, wherewith the image component represents a virtual retina and/or virtual surroundings.

2. The ophthalmoscope simulator according to claim 1; wherein at least one video camera for generating video images of the real surroundings is provided on the support, and the video image can represent at least a part of the surroundings.

3. The ophthalmoscope simulator according to claim 2; wherein the support, the video camera, the ophthalmoscope dummy, the patient head dummy, the patient eye position, and/or the peripheral surface each bear at least one marker whereby the spatial position and/or orientation relative to the position recognition system can be determined, via said position recognition system.

4. The ophthalmoscope simulator according to claim 2; wherein a second display is provided, wherewith the first display may be positioned ahead of the right eye of the observer and the second display may be positioned ahead of the left eye of the observer, and wherewith a distance a4 between the displays is adjustable.

5. The ophthalmoscope simulator according to claim 4; wherein a second video camera is provided, the image from which is displayable via the second display, wherewith a distance a5 between the video cameras is adjustable.

6. The ophthalmoscope simulator according to claim 4; wherein the images, image components, and/or video images stored or changed in the computer can be displayed on the at least one first image display or on a separate monitor provided for such displaying.

7. The ophthalmoscope simulator according to claim 2; wherein the computer comprises a device for storing, retrieving, evaluating, and/or changing of images and/or image components, and for combination of image components of regions which the observer has observed on the virtual retina during a simulated examination.

8. The ophthalmoscope simulator according to claim 1; wherein the ophthalmoscope dummy is a dummy for a lens of an indirect ophthalmoscope or a dummy for a direct ophthalmoscope.

9. The ophthalmoscope simulator according to claim 1; wherein a device for simulation of a light filter are provided.

10. The ophthalmoscope simulator according to claim 1; wherein a device for representation of a distance (a1, a2, and/or a3) and/or device for representation of a deviation of the distance (a1, a2, and/or a3) from a set-point value are provided, wherewith the distance a1 is the distance between the support and the patient eye position, the distance a2 is the distance between the ophthalmoscope dummy and the patient eye position, and the distance a3 is the distance between the support and the ophthalmoscope dummy.

11. The ophthalmoscope simulator according to claim 10; wherein the device comprises an optical display which are perceptible via the at least one first image display.

12. A method of operating an ophthalmoscope simulator comprising a support which can be applied to the head of an observer, which support bears at least one first image display, which display can be positioned ahead of one eye of the observer for representation of a virtual reality, a position recognition system whereby a spatial position and/or orientation or relative position of the support is determinable, and a computer whereby an image of the surroundings and/or of a patient head can be displayed to the observer via the at least one first image display; wherein the simulator further comprises an ophthalmoscope dummy and a patient head dummy, wherewith the patient head dummy has at least one peripheral surface bearing a patient eye position, wherewith by the position recognition system the spatial position and/or orientation of the ophthalmoscope dummy and/or of the patient head dummy can be determined; and wherein an image component can be superimposed in the image displayed to the observer, in addition to or alternatively to the image of the ophthalmoscope dummy, wherewith the image component represents a virtual retina and/or virtual surroundings comprising the steps of:

determining the spatial position and/or orientation of the ophthalmoscope dummy, the patient head dummy, and the support by the position recognition system;

displaying an image of surroundings, a patient head, and or the ophthalmoscope dummy on the at least one first image display; and superimposing an image component which virtually represents the retina in the image, in addition to or alternatively to the image component of the ophthalmoscope dummy.

13. The method according to claim 12; wherein the image component representing the retina is only superposed if the relative positions between the support, the ophthalmoscope dummy, and the patient head dummy satisfy predetermined conditions.

14. The method according to claim 12; wherein by a video camera, the video mage of real surroundings, as well as of the patient head dummy, a hand of the observer, the ophthalmoscope dummy, and/or a part of same, is obtained and is displayed on the at least one first image display.

15. The method according to claim 12; wherein a distance a1 between the support and the position of the patient eye, and/or a distance a2 between the ophthalmoscope dummy and the position of the patient eye, and/or a distance a3 between the support and the ophthalmoscope lens dummy, and/or a deviation of one or more of a1, a2, a3 from a set-point value, is/are displayed to the observer.

16. The method according to claim 12; wherein for the position and/or movement of the support and/or of the ophthalmoscope dummy, images are computed which represent the view from at least one other viewpoint in space.

17. The method according to claim 12; wherein eye movements of the patient are simulated.

18. A computer program product embodied in a non-transitory computer readable medium executable by a processor capable of carrying out the method according to claim 12.

* * * * *